United States Patent [19]

Coupland et al.

[11] 4,176,074

[45] Nov. 27, 1979

[54] MOLYBDENUM COMPLEXES OF ASHLESS OXAZOLINE DISPERSANTS AS FRICTION REDUCING ANTIWEAR ADDITIVES FOR LUBRICATING OILS

[75] Inventors: Keith Coupland; Juan M. Salva, both of Sarnia; Clinton R. Smith, Camlachie, all of Canada

[73] Assignee: Exxon Research & Engineering Co., Florham Park, N.J.

[21] Appl. No.: 943,342

[22] Filed: Sep. 18, 1978

[51] Int. Cl.$^2$ .................. C10M 1/48; C10M 1/54; C10L 1/30; C07F 11/00

[52] U.S. Cl. .................. 252/32.7 E; 44/63; 44/68; 252/49.7; 548/110; 548/101

[58] Field of Search .................. 252/32.7 E, 49.7; 260/299; 44/63, 68

[56] References Cited

U.S. PATENT DOCUMENTS

| | | | |
|---|---|---|---|
| 2,450,806 | 10/1948 | McCarthy | 252/49.7 |
| 2,450,807 | 10/1948 | McCarthy | 252/49.7 |
| 4,035,309 | 7/1977 | Brois | 252/49.7 |
| 4,062,786 | 12/1977 | Brois et al. | 252/51.5 R |
| 4,102,798 | 7/1978 | Ryer et al. | 252/51.5 A |

FOREIGN PATENT DOCUMENTS

882295 11/1961 United Kingdom .................. 252/49.7

*Primary Examiner*—Irving Vaughn
*Attorney, Agent, or Firm*—Roland A. Dexter

[57] ABSTRACT

An oil-soluble molybdenum complex of an ashless oxazoline dispersant, preferably an oil-soluble reaction product of a molybdenum compound such as molybdic oxide with 0.5 to 1 molar equivalent of a hydrocarbon substituted mono- and bisoxazolines obtained as a reaction product of hydrocarbyl substituted dicarboxylic acid, ester, or anhydride, for example, polyisobutenyl-succinic anhydride with from 1 to 2 molar equivalents of a 2,2-disubstituted-2-amino-1-alkanols, such as tris-(hydroxymethylamino)methane (THAM), is a useful additive to a lubricating oil since both the sludge dispersant and antifriction properties of said oil are enhanced.

17 Claims, No Drawings

MOLYBDENUM COMPLEXES OF ASHLESS OXAZOLINE DISPERSANTS AS FRICTION REDUCING ANTIWEAR ADDITIVES FOR LUBRICATING OILS

BACKGROUND OF THE INVENTION

The present invention concerns oil-soluble molybdenum complexes of oxazoline dispersants, their method of preparation, and the utility of oil-soluble molybdenum oxazoline dispersants as lubricating oil additives, which markedly improve the sludge dispersancy-friction reducing properties of lubricating oils employed for crankcase lubrication of internal combustion engines.

There are two principle environments which are encountered by automotive crankcase lubricants, i.e. cyclical high and low temperatures from stop-and-go driving and continuous high temperatures from extended operation of the automobile over long distances. Each of these environments provokes the presence in the lubricant of varying proportions of foreign particles such as dirt, soot, water and decomposition products resulting from breakdown of the oil. This foreign matter appears responsible for the deposition of a mayonnaise-like sludge which circulates with the oil.

During the past decade, ashless sludge dispersants have become increasingly important, primarily in improving the performance of lubricants in keeping the engine clean of deposits and permitting extended crankcase oil drain periods while avoiding the undesirable environmental impact of the earlier used metal-containing additives. One commercial type of ashless dispersant contains nitrogen resulting from the attachment of an amine or polyamine to a long-chain hydrocarbon polymer (the oil solubilizing portion of the molecule), usually polyisobutylene through an acid group, e.g. polyisobutenyl succinic anhydride, by forming amide or imide linkages. Other known dispersants include the reaction products of hydrocarbon substituted succinic anhydride, e.g., polyisobutenylsuccinic anhydride, with compounds containing both an amine group and a hydroxy group such as in United Kingdom Pat. No. 984,409 which teaches ashless, amide/imide/ester-type lubricant additives prepared by reacting an alkenylsuccinic anhydride, said alkenyl group having 30 to 700 carbon atoms, with a hydroxy amine including THAM. In contrast to the foregoing, United Kingdom Pat. No. 1,483,681-2 teach that the reaction of a hydrocarbyl dicarboxylic acid material, i.e. acid or anhydride, or ester, with certain classes of amino alcohols, under certain conditions including metal salt promotion, will result in products containing one or two heterocyclic ring structures, namely, an oxazoline ring, and that products containing at least one oxazoline ring can be tailored for various functions, such as antirust agents, detergents, or dispersants for oleaginous compositions including lube oil, gasoline, turbine oils and oils for drilling applications.

In the operation of an internal combustion engine, there are many "Boundary Lubrication" conditions where two rubbing surfaces must be lubricated, or otherwise protected, so as to prevent wear and to insure continued movement. Moreover, where, as in most cases, friction between the two surfaces will increase the power required to effect movement and where the movement is an integral part of an energy conversion system, it is most desirable to effect the lubrication in a manner which will minimize this friction and/or reduce wear. As is also well known, both wear and friction can be reduced, with various degrees of success, through the addition of a suitable additive or combination thereof, to a natural or synthetic lubricant. Similarly, continued movement can be insured, again with varying degrees of success, through the addition of one or more appropriate additives.

While there are many known lubricant additives which may be classified as antiwear, antifriction and extreme pressure agents and some may in fact satisfy more than one of these functions as well as provide other useful functions but rarely if ever dispersancy, it is also known that many of these additives act in a different physical or chemical manner and often compete with one another, e.g. they may compete for the surface of the moving metal parts which are subjected to lubrication. Accordingly, extreme care must be exercised in the selection of these additives to insure compatibility and effectiveness.

The metal dihydrocarbyl dithiophosphates, e.g. the zinc dialkyl dithiophosphates, are one of the additives which are known to exhibit antioxidant and antiwear properties. While they afford excellent oxidation resistances and exhibit superior antiwear properties, it has heretofore been believed that the same increases or significantly limits their ability to decrease friction between moving surfaces. As a result, compositions containing zinc dialkyl dithiophosphates were not believed to provide the most desirable lubricity and, in turn, it was believed that use of compositions containing the same would lead to significant energy losses in overcoming friction even when antifriction agents are included in the composition.

Known ways to solve the problem of energy losses due to high friction in crankcase lubrication include the use of synthetic ester base oils which are expensive and the use of insoluble molybdenum sulfide and graphite dispersions which have the disadvantage of giving the oil composition a black or hazy appearance. It would be desirable then to provide oil-soluble molybdenum compounds and thus overcome the disadvantage. Oil-soluble molybdenum additives taught as useful in lubricating oils include the molybdates of organic nitrogen bases obtained from heating an aqueous solution of molybdic acid and an aliphatic amine or heterocyclic nitrogen base (see U.S. Pat. No. 3,144,712).

The practical exploitation of various types of molybdenum compounds and complexes as lubricant additives has been hindered not only by their insolubility and/or corrosiveness but also by low thermal stability.

SUMMARY OF THE INVENTION

It has now been discovered that ashless oxazoline dispersants can be reacted with a source of molybdenum to provide a molybdenum-containing ashless dispersant of improved thermal stability in hydrocarbons, preferably lubricating oils and having the property of importing enhanced lubricity to said lubricating oil. This has been accomplished by use of an aqueous-nonaqueous reaction medium. The operational embodiment of the invention thus is a lubricating oil composition comprising a major proportion of mineral oil and a minor but at friction reducing amount of an oil-soluble molybdenum-containing ashless oxazoline lubricating oil dispersant, said dispersant having from 0.5 to 20 wt.% molybdenum based on the weight of said dispersant and further characterized by from one to two oxazoline rings and a substantially saturated hydrocarbon group containing at least about 50 carbon atoms.

These materials are prepared from conventional ashless oxazoline dispersants by reaction of said dispersant with a molybdenum source compound in a binary solvent system comprising an aqueous component of the class consisting of water and ammonium hydroxide and a non-aqueous component consisting of the class consisting of tetrahydrofuran (THF) and a hydrocarbon boiling between 70° and 250° C. The volume ratio of aqueous to non-aqueous component ranges from 1:1000 to 1:1, preferably 1:100 to 1:4, optimally 1:10. In the context of this invention, the aqueous component can be considered a promoter for the molybdation of the oxazoline dispersant. Thus, for the purposes of this discussion, both the water and the ammonium hydroxide could be defined as an essential promoter of molybdation in a non-aqueous reaction medium.

It has now been further discovered that a stable molybdenum complex can be obtained with little if any destruction of the ashless dispersant when complexing is effected at a temperature of 40° C. to 250° C., preferably from 50° to 200° C., in said binary solvent system.

In accordance with the present invention, it is preferred that the lubricity enhancing, i.e. friction reducing, additive is present in the mineral oil in an amount to provide from about 0.01 to 2.0, preferably 0.02–1.0 and optimally 0.05–0.5 weight percent molybdenum in said oil. All weight percent being based on the total weight of the lubricating composition.

In preferred form, the molybdenum complex is that of an oxazoline dispersant additive derived from the reaction of one mole of a $C_8$ to $C_{400}$ hydrocarbyl substituted dicarboxylic acid material such as poly(isobutenyl) succinic anhydride wherein said hydrocarbyl substituent e.g. the poly(isobutenyl) group has a $(\overline{M}_n)$ ranging from about 700 to 5,600, optimally from about 900 to 1600 with from one to two, preferably 1.5 to 2, molar equivalents of a 2,2-disubstituted-2-amino-1-alkanol having 2 to 3 hydroxy groups and containing a total of 4 to 8 carbon atoms usefully by heating at a temperature of from 140° C. to 240° C. until cessation of water evolution; said additive being complexed with from 1 to 2 molar equivalents of molybdic oxide, i.e. $MoO_3$ and containing from 0.5 to 20, preferably 2 to 10, optimally 5, wt.% molybdenum.

DETAILED DESCRIPTION OF THE INVENTION

Generally the hydrocarbyl substituted dicarboxylic acid material, i.e. acid or anhydride or ester which is used to produce the oxazoline dispersants for complexing with molybdenum includes alpha-beta unsaturated $C_4$ to $C_{10}$ dicarboxylic acid, or anhydrides or esters thereof, such as fumaric acid, itaconic acid, maleic acid, maleic anhydride, chloromaleic acid, dimethyl fumarate, etc., which are substituted with a hydrocarbyl group, usefully a hydrocarbon chain containing at least 50 carbons (branched or unbranched) and includes long hydrocarbon chains, generally an olefin polymer chain, whereby useful oil-solubility is provided.

In general, these hydrocarbyl substituted dicarboxylic acid materials and their preparation are well known in the art, for example see U.S. Pat. Nos. 3,219,666; 3,172,892; 3,272,746; the aforementioned prior art patents; as well as being commercially available, e.g., polyisobutylene succinic anhydride.

The dicarboxylic acid material can be illustrated by an alkenyl substituted anhydride which may contain a single alkenyl radical or a mixture of alkenyl radicals variously bonded to the cyclic succinic anhydride group with the alkenyl substituent containing from 8 to 400 carbons and preferably from 50 to 300 carbons. The anhydrides can be obtained by well-known methods, such as the Ene reaction between an olefin and maleic anhydride or halo-succinic anhydride or succinic ester (U.S. Pat. No 2,568,876).

Suitable olefins include octene, decene, dodecene, tetradecene, hexadecene, octadecene, eicosene, and polymers of propylene, butene, isobutene, pentene, decene and the like, and halogen-containing olefins. The olefins may also contain cycloalkyl and aromatic groups.

With 2-chloromaleic anhydride and related acylating agents, alkenylmaleic anhydride reactants are formed. Derivatization of these reactants also afford useful oxazoline products which can be molybdated.

Preferred olefin polymers for reaction with the unsaturated dicarboxylic acids are polymers comprising a major molar amount of $C_2$ to $C_5$ monoolefin, e.g., ethylene, propylene, butylene, isobutylene and pentene. The polymers can be homopolymers such as polyisobutylene, as well as copolymers of two or more of such olefins such as copolymers of: ethylene and propylene; butylene and isobutylene; propylene and isobutylene; etc. Other copolymers include those in which a minor amount of the copolymer monomers, e.g., 1 to 20 mole % is a $C_4$ to $C_{18}$ non-conjugated diolefin, e.g., a copolymer of isobutylene and butadiene; or a copolymer of ethylene, propylene and 1,4-hexadiene; etc.

The olefin polymers will usually have $(\overline{M}_n)$s within the range of about 700 and about about more usually between about 900 and abut 5,600. Particularly useful olefin polymers have $(\overline{M}_n)$s of about 1200 to 5000 with approximately one terminal double bond per polymer chain. An especially valuable starting material for a highly potent dispersant additive are polyalkenes e.g., polyisobutylene, having about 90 carbons.

OIL-SOLUBLE OXAZOLINE DISPERSANT

Generally, useful oil-soluble oxazoline reaction products and their methods of preparation are fully described in United Kingdom Pat. No. 1,483,681-2 which are fully incorporated herein by reference thereto. This oxazoline dispersant which forms a portion of the inventive combination can be characterized in its preferred form as an oil-soluble product obtained from heating together a molar equivalent of a hydrocabon substituted $C_4$–$C_{10}$ dicarboxylic acid material having more than about 50 carbon atoms per dicarboxylic acyl group and from 1 to 2, preferably 1.5 to about 2, molar equivalents of a 2,2-di-substituted-2-amino-1-alkanol having 2 to 3 hydroxy groups and containing a total of 4 to 8 carbons at a temperature of from about 140° C. to 240° C. until cessation of water evolution indicating completion of the oxazoline reaction. This referenced amino-alkanol which readily produces the oxazoline rings requisite for this dispersant according to this invention can be represented by the formula

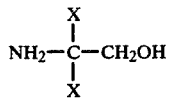

wherein X is an alkyl, or hydroxy alkyl group, with at least one of the X substituents being a hydroxy alkyl group of the structure —$(CH_2)_nOH$, wherein n is 1 to 3.

Examples of such 2,2-disubstituted amino-alkanols, include 2-amino-2-methyl-1,3-propanediol, 2-amino-2-(hydroxymethyl)-1,3-propanediol (also known as tris(hydroxymethyl) aminomethane or THAM), 2-amino-2-ethyl-1,3-propanediol, etc. Because of its effectiveness, availability and cost, the THAM is particularly preferred. It is to be noted that other amino alcohols such as ethanolamine, propanolamine and butanolamine which lack the 2,2-disubstitution, do not afford the oxazoline product. The requisite ($\overline{M}_n$) ranges of these products have already been specified.

The formation of the preferred oxazoline dispersants in high yield, can be effected by adding about 1.0 (to obtain the monooxazoline) to about 2 (to obtain the bisoxazoline) mole equivalent of the aforesaid 2,2-disubstituted-2-amino-1-alkanol per mole equivalent of the dicarboxylic acid material, with or without an inert diluent, and heating the mixture at 140°–240° C., preferably 160°–205° C., optimally 170°–190° C. for ½ to 24, more usually 2 to 8 hours, until the reaction is complete.

Completion of the oxazoline reaction can be readily ascertained by using periodic infrared spectral analysis for following oxazoline formation (oxazoline peak forms at 6.0 microns), or by the cessation of water evolution of about 1.5 to 3.0 moles of water.

Although not necessary, the presence of small amounts, such as 0.01 to 2 wt.%, preferably 0.1 to 1 wt.% based on the weight of the reactants, of a metal salt e.g. zinc acetate can be used in the reaction mixture as a catalyst.

Inert solvents which may be used in the oxazoline reaction include hydrocarbon oils, e.g., mineral lubricating oil, kerosene, neutral mineral oils, xylene, halogenated hydrocarbons, e.g., carbon tetrachloride, dichlorobenzene, tetrahydrofuran, etc. Such solvents can be used in molybdation condensation or complexing reaction with said oxazoline dispersant.

While not known with complete certainty, it is believed that the reaction of the hydrocarbyl substituted dicarboxylic acid material, e.g., a substituted succinic anhydride with the amino alcohol of the invention, e.g., about 1.5 to 2 equivalents of 2,2-disubstituted-2-aminomethanol such as tris-hydroxymethylaminomethane (THAM), gives oxazoline, e.g. a mixture of monooxazoline and bisoxazoline to all bisoxazoline via the intermediacy of several discrete reaction species such as a hemiester and an amic acid amine salt which upon heating goes to the final bisoxazoline product.

OIL-SOLUBLE BORATED OXAZOLINE DISPERSANTS

It is possible to molybdate either the oxazoline dispersant or its borated derivative as is described in U.S. Patent Application 763,545, U.S. Pat. No. 4,116,876, filed Jan. 28, 1977 (of common assignee with this application) by reaction with a molybdenum source.

To further enhance the dispersancy of oxazoline dispersants, the said dispersant, e.g. the alkenyl succinic bisoxazoline, is readily borated by treating said oxazoline dispersant with a boron compound selected from the class consisting of boron oxide, boron halides, boron acids and esters of boron acids in a molar ratio of 1:1 to 1:2 of oxazoline dispersant to boron compound.

Borating is readily carried by adding from about 1 to 3 wt. % (based on the weight of said oxazoline compound) of said boron compound, preferably boric acid which is most usually added as a slurry to said oxazoline dispersant and heating with stirring and at from about 135° C. to 165° C. for from 1 to 5 hours followed by nitrogen stripping at said temperature ranges and filtration if desired.

The resulting borated oxazolines contain from about 0.1 to 2.0, preferably 0.2 to 0.8, wt. % boron based on the total weight of the borated oxazoline compound. The boron, which appears to be in the reactant dispersant as dehydrated boric acid polymers (primarily $HBO_2)_3)$, attaches chemically to the dispersant imides and diimides as amine salts e.g. the metaborate salt of said diimide and appears not displaced in the molybdenumization step.

Oxazoline formation from the dicarboxylic acid material is usefully carried as a solution reaction with the dicarboxylic acid material, e.g. polyisobutenylsuccinic anhydride dissolved in a solvent such as mineral oil to which the other reactant is added. The formation of the oxazoline dispersants in high yield can be effected by adding from about 1 to 2, preferably about 1.5 to 2.0, molar proportions of said amino alkanol per molar proportion of dicarboxylic acid and thereafter heating the system within the appropriate temperature range until the appropriate amount of water of reaction is evolved. Typically the solvent mineral oil is adjusted so that if constitutes 50% weight of the final oxazoline dispersant solution. This solution can be readily used for boration as described.

MOLYBDENUM SOURCE

The source of molybdenum is a molybdenum oxygen or sulfur-containing compound capable of complexing with the ashless dispersant to provide a thermally stable molybdenum complex containing from about 0.5 to 20, preferably 2 to 10, optimally about 5wt.% molybdenum based on the total weight of said complex. The sources of molybdenum include molybdic trioxide (preferred) also known as molybdic anhydride, ammonium thiomolybdate, ammonium bismolybdate, molybdenum halides, and ammonium heptamolybdate tetrahydrate.

METHOD OF PREPARING THE COMPLEX

The molybdenum oxazoline complex is substantially the product of a binary solution reaction between 1–3 moles of oxazoline dispersant (either the borated or non-borated) and 1 mole of molybdenum metal derived from the molybdenum source. The reaction is readily carried out by reaction at an elevated temperature of from 40° C. to 250° C., preferably 50° C. to 200° C. optimally 60° C. to 180° C. The reaction is carried out in a binary solution system wherein water is present (either as water or ammonium hydroxide) along with a non-aqueous component such as tetrahydrofuran (THF) or a hydrocarbon boiling between 70° C. and 250° C. and as preferred a second non-aqueous component which is a higher boiling point hydrocarbon as mineral oil. A highly useful reaction system is 1 to 20% water, ammonium hydroxide and mixtures thereof, 20 to 60% mineral oil and the balance xylene, toluene or tetrahydrofuran.

The reaction is carried out over a period of from about 4 to 20, preferably 6 to 12, hours in order to suitably stabilize the complex after which the binary solvents are generally removed and the complex dissolved in mineral oil for ease of handling.

Carrying out the organo molybdenum complexing reaction in a binary solvent system of one part by weight water or ammonium hydroxide per 1 to 1000 parts by weight of THF or said lower boiling hydrocarbon provides a number of benefits over a reaction without solvent or in a light aromatic solvent such as toluene or a light hydrocarbon oil, e.g. mineral oil including: faster reaction time; completion of reaction to a stabilized molybdenum complex at a lower temperature; and, an additive product solution which when added to lubricating oil provides both enhanced friction reduction and sludge dispersancy.

SULFUR DONORS

The hydrocarbon-soluble molybdenum complexes of oxazoline dispersants provide not only dispersancy for lubricating oils but enhanced lubricity as well as when used in combination with an active sulfur donor which can be defined as a compound which when used in admixture with the dispersant-molybdenum complex reduces the coefficient of friction at least about 10% relative to that provided by the complex alone. The active sulfur donor is present in an amount of from about 0.1 to 10, preferably 0.2 to 2, parts by weight per part by weight of molybdenum complex.

Illustrative of active sulfur donors are metal dihydrocarbyl dithiophosphates and the corresponding precursor esters, phosphosulfurized pinenes, sulfurized olefins and hydrocarbons, sulfurized fatty esters and sulfurized alkyl phenols.

Preferred are the zinc dihydrocarbyl dithiophosphates which are salts of dihydrocarbyl esters of dithiophosphoric acids and may be represented by the following formula:

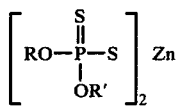

wherein R and R' may be the same or different hydrocarbyl radicals containing from 1 to 18 and preferably 2 to 12 carbon atoms and including radicals such as alkyl, alkenyl, aryl, aralkyl, alkaryl and cycloaliphatic radicals. Particularly preferred as R and R' groups are alkyl groups of 2 to 8 carbon atoms. Thus, the radicals may, for example, be ethyl, n-propyl, i-propyl, n-butyl, i-butyl, sec-butyl, tert-butyl, amyl n-hexyl, i-hexyl, n-heptyl, n-octyl decyl, dodecyl, octadecyl, 2-ethylhexyl, phenyl, butylphenyl, cyclohexyl, methylcyclopentyl, propenyl, butenyl, etc. In order to obtain oil solubility, the total number of carbon atoms in the dithiophosphoric acid will average about 5 or greater.

The zinc dihydrocarbyl dithiophosphates which are useful as the coadditive, i.e. sulfur donor of the present invention may be prepared in accordance with known techniques by first esterifying a dithiophosphoric acid usually by reaction of an alcohol or phenol with $P_2S_5$ and then neutralizing the dithiophosphoric acid ester with a suitable zinc compound such as zinc oxide.

In general, the zinc dihydrocarbyl dithiophosphate will be used in the lubricating composition at a concentration within the range of about 0.01 to about 5 parts by weight per 100 parts of lubricating oil and preferably from about 0.5 to about 1.5. This is adequate for sulfur donation whereby the lubricity enhancement of the lubricating oil composition by the coadditive combination is realized.

As noted earlier, an equally suitable active sulfur donor is the dihydrocarbyl esters of dithiophosphoric acid which may be represented by the formula:

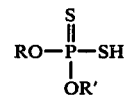

where R and R' are as previously defined. Particularly useful is the dibutylphenyl dithiophosphate.

The phosphorosulfurized terpenes as represented by pinene, dipenene, allo-ocimene, etc., are another group of dithiophosphate diesters which are active sulfur donors. Of the terpenes, the bicyclic pinene is preferred. The phosphosulfurized terpene is readily obtained by reaction of about one mole of diester of thiophosphoric acid and one mole of pinene at a temperature of at least 100° C., e.g. 100° C. to 200° C. The preferred active sulfur donor can be characterized as the bornyl ester of dihydrocarbyl ($C_2$–$C_{20}$) dithiophosphoric acids (as shown in U.S. Pat. No. 2,689,258).

The sulfurized olefins and hydrocarbons are further esters of thiophosphoric acids which are useful sulfur donors. These esters are achieved by reaction with olefins such as ethylene, propylene, isobutylene, decene, dodecene, octadecene, etc., olefin polymers of molecular weight ranging from 100 to 50,000 such as ethylene, propylene, isobutylene, etc., aromatics such as benzene, naphthylene, toluene, xylene, etc., petroleum fractions and condensation products of halogenated aliphatic hydrocarbons with aromatic compounds, e.g. wax naphthalene (see U.S. Pat. No. 2,804,431).

The sulfurized fatty esters are another subclass of esters which are active sulfur donors. These products are readily obtained from the reaction of $P_2S_5$ and aliphatic alcohols usefully having from about 8 to 22 carbons obtained from natural sources including linoleic, palmolitic, behenic, stearic, palmitic, lauric, capric, etc., as well as mixtures obtained from vegetable and animal oils such as tall oil.

The sulfurized alkyl phenols are generally $C_4$ to $C_{20}$ alkyl phenol sulfides. These sulfurized alkyl phenols are readily produced by sulfurizing an alkyl phenol with a sulfur halide or elemental sulfur.

OTHER ADDITIVES FOR LUBRICATING COMPOSITIONS

In addition to the molybdenum complex of the oxazoline dispersant and active sulfur donor, the lubricating oil composition may contain other well-known lubricating oil additives to provide trouble-free operation of the lubricateed equipment, such as ashless dispersants, metallic detergents, supplemental oxidation and corrosion inhibitors, extreme pressure agents, rust inhibitors, pour point depressants, viscosity index improvers, etc.

1. ASHLESS DISPERSANTS

As used herein, the terminology "ashless dispersant" in describing both the reactant and the additive is intended to describe the now well-known class of non-metal-containing oil-soluble polymeric additives or the acyl derivatives of relatively high molecular weight carboxylic acids which are capable of dispersing contaminants and the like in hydrocarbons such as lubricating oils. The carboxylic acids may be mono- or polycarboxylic acids and they are generally characterized by substantially hydrocarbon constituents containing an average of 50 to 250 aliphatic carbon atoms.

A preferred class of ashless dispersants are the nitrogen-containing dispersant additives which are generally known in the art as sludge dispersants for crankcase motor oils. These dispersants include mineral oil-soluble salts, amides, imides and esters made from high molecular weight mono- and dicarboxylic acids (and where they exist the corresponding acid anhydrides) and various amines of nitrogen-containing materials having amino nitrogen or heterocyclic nitrogen and at least one amido or hydroxy group capable of salt, amide, imide or ester formation. Usually, these dispersants are made by condensing a monocarboxylic acid or a dicarboxylic acid of anhydride, preferably a succinic acid producing material such as alkenyl succinic anhydride, with an amine or alkylene polyamine. Usually, the molar ratio of acid or anhydride to amine is between 1:1 to 5:1, e.g. 1 mole of $C_{10}$-$C_{100}$ polyisobutenyl succinic anhydride to 2 moles of tetraethylene pentamine.

Primarily because of its ready availability and low cost, the hydrocarbon portion of the mono-, or dicarboxylic acid or anhydride is preferably derived from a polymer of a $C_2$ to $C_5$ monoolefin, said polymer generally having between 50 and 250 carbon atoms. A particularly preferred polymer is polyisobutylene.

Polyalkyleneamines are usually used to make the non-metal-containing dispersant. These polyalkyleneamines include those represented by the general formula:

$NH_2(CH_2)_n-[NH(CH_2)_n]_m-NH_2$ wherein n is 2 to 3 and m is a number from 0 to 10. Specific compounds coming within the formula include diethylenetriamine, tetraethylenepentamine, dipropylenetriamine, octaethylenenonamine, and tetrapropylenepentamine; N,N-di-(2-aminoethyl) ethylenediamine may also be used. Other aliphatic polyamino compounds that may be used are N-aminoalkylpiperazines, e.g. N-(2-aminoethyl) piperazine. Mixtures of alkylene polyamines approximating tetraethylene pentamine are commercially available, e.g. Dow E-100 sold by Dow Chemical Company of Midland, Michigan.

Representative dispersants are formed by reacting about one molar amount of polyisobutenyl succinic anhydride with from about one to about two molar amounts of tetraethylene pentamine or with from about 0.5 to 1 moles of a polyol, e.g. pentaerythritol.

It is possible to modify the ashless dispersants generally by the addition of metals such as boron in order to enhance the dispersancy of the additive. This is readily accomplished by adding boric acid to the reaction mixture after the imidation or esterification is substantially complete and heating the mixture at temperatures of 100 to 150° C. for a few hours.

2. OTHER ADDITIVES

Detergents useful in conjunction with dispersants, preferably the ashless type, include normal, basic or overbased metal, e.g. calcium, magnesium, etc., salts of petroleum naphthenic acids, petroleum sulfonic acids, alkyl benzene sulfonic acids, oil-soluble fatty acids, alkyl salicyclic acids, alkylene-bis-phenols, and hydrolyzed phosphorosulfurized polyolefins.

Oxidation inhibitors include hindered phenols, e.g. 2,6-ditert. butyl para-cresol, amines, sulfurized phenols and alkyl phenothiazines.

Pour point depressants include wax alkylated aromatic hydrocarbons, olefin polymers and copolymers, acrylate and methacrylate polymers and copolymers.

Viscosity Index Improvers include olefin polymers such as polybutene, ethylene-propylene copolymers, hydrogenated polymers and copolymers and terpolymers of styrene with isoprene and/or butadiene, polymers of alkyl acrylates or alkyl methacrylates, copolymers of alkyl methacrylates with N-vinyl pyrollidone or dimethylaminoalkyl methacrylate, post-grafted polymers of ethylene-propylene with an active monomer such as maleic anhydride which may be further reacted with an alcohol or an alkylene polyamine, styrene/maleic anhydride polymers post-reacted with alcohols and amines, etc.

The hydrocarbons in which the additive combination of the invention is most effective are mineral oils having a viscosity as measured by ASTM D-445 of from about 2 to 40, preferably 5 to 20 centistokes at 99° C.

If the molybdenum-containing oxazoline dispersant is used as an additive concentrate, the concentrate may consist essentially of from about 5 to 80 weight percent of molybdenum containing dispersant, based on the total weight of said concentrate, the remainder being a suitable solvent such as kerosene, mineral oil, synthetic oil and a naphtha or the like. The preferred concentrate contains about 10–60 weight percent of the additive combination in the solvent.

Whether the molybdenized oxazoline dispersant is used alone or in combination with other additives, its concentration may vary appreciably with the particular application. For example, when the said molybdenum containing dispersants are used alone in a fuel such as gasoline, the concentration of the additive ranges from 1 to 1000, preferably 5–50 parts per million, based on the total weight of the gasoline. In a lubricant, however, it is used from about 0.1 to 20 preferably 0.5–5% based on the total weight of the oil.

The invention will be further understood by reference to the following Examples which illustrate a preferred form of the invention and compares the same with different, though similar compositions.

The following Examples illustrate more clearly the compositions of the present invention. However, these illustrations are not to be interpreted as specific limitations on this invention.

EXAMPLE 1

A mixture of 40 grams of a 50 wt.% mineral oil solution of a bisoxazoline dispersant [obtained from the reaction of one mole of polyisobutenyl ($\overline{M}_n$ of ~ 1300) succinic anhydride with about two moles of tris-(hydroxymethyl) aminomethane (THAM) to provide the bisoxazoline of polyisobutenyl succinic anhydride], 2.87 grams of molybdic oxide ($MoO_3 \cdot H_2O$), 50 cc of toluene and 5 cc of water were refluxed with stirring for 7.25 hours. During this time, water and xylene were removed by distillation. The reactants were freed from solid material by filtration and the filtrate stripped of volatile material by rotoevaporation. The product was a dark brown oil containing 3.56% molybdenum. This represents a conversion, based on molybdenum, of 79% on theory.

EXAMPLE 2

The molybdated dispersant of EX. 1 was evaluated, in a formulated oil, for its effect on friction in a Roxana Four-Ball Tester. As a comparative example, an oil containing the dispersant but without molybdenum was run. The concentration of the molybdenum-containing dispersant was adjusted to provide 0.1% molybdenum in the oil. A total dispersant concentration of 2.5% was maintained in all tests.

The lubricant composition was:

| Component | Wt % Active Ingredient |
|---|---|
| Dispersant | 2.5 |
| Magnesium Sulfonate (overbased) | 0.4 |
| Zinc dinonyl phenoxy dithiophosphate | 1.0 |
| Mineral oil | 96.1 |

The Roxana Four-ball wear tester with the Brown/GE modification from Roxana Machine Works, St. Louis, MO was used to measure friction properties by the following procedure. The tester was assembled in the normal wear procedure as described in ASTM D2266-67 using four ½" bearing steel balls. The tester was brought to 110° C. and run at 1200 rpm and 15 kg for a minimum of 45 minutes. If the frictional force as seen on the strip chart recorder is constant for the last 10 minutes, the speed is reduced to 25 rpm. Otherwise, the test is carried on until frictional force has stabilized. The test at 25 rpm is carried out at 110° C. and 15 kg for 15 minutes or until frictional force has stabilized.

The compound of the invention was evaluated by subjecting the product of Example 1 to a study of its utility as a lubricity enhancing and/or antiwear additive for lubricating oils by using said Testing Procedure.

The results of tests under said Testing Procedure A are set forth in Table I.

From the foregoing, it is shown that the molybdenum-containing dispersant additives of the invention provide lubricity enhancement to lubricating oils superior to their non-molybdized counterparts when an active sulfur donor is present and that they have utility as additives for lubricating oils providing both sludge dispersancy and lubricity enhancement.

It is to be understood that the Examples present in the foregoing specification are merely illustrative of this invention and are not intended to limit it in any manner; nor is the invention to be limited by any theory regarding its operability. The scope of the invention is to be determined by the appended claims.

TABLE 1

COMPARISON OF MOLYBDENUM CONTAINING DISPERSANTS FOR FRICTION REDUCTION

| Test # | Molybdate Product of Example # | Weight % Active Ingredient* | Dispersant of Example # | Weight % Active Ingredient | Coefficient of Friction[1] | | Friction Reduction[2] | |
|---|---|---|---|---|---|---|---|---|
| | | | | | 1200 rpm | 50 rpm | 1200 rpm | 50 rpm |
| 1 | — | — | 1 | 2.5 | 0.096 | .106 | — | — |
| 2 | 1 | 1.9 | 1 | 1.1 | 0.053 | 0.045 | 45 | 58 |

[1]15 kg load
[2]Relative to base case
*This was based upon the product oil of Example 1 which contained 50 wt. % mineral oil and 50 wt. % molybdenum containing dispersant.

What is claimed is:

1. An oil-soluble molybdenum complex of an ashless oxazoline dispersant having from 0.5 to 20 wt.% molybdenum based on the weight of said dispersant.

2. An oil-soluble molybdenum complex according to claim 1 wherein said dispersant is an oxazoline compound having an oil-solubilizing group in the form of a long chain hydrocarbon group attached to an acid group so the substituted acid contains a total of 50 to 400 carbon atoms.

3. The complex according to claim 2 wherein said complex is the reaction product of a molybdenum compound with 0.5 to 1 molar equivalent of a $C_8$ to $C_{400}$ hydrocarbon substituted mono- and bisoxazoline obtained as a reaction product of hydrocarbyl substituted dicarboxylic acid, ester, or anhydride, with from 1 to 2 molar equivalents of a 2,2-disubstituted-2-amino-1-alkanol represented by the formula

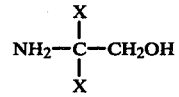

wherein X is an alkyl or hydroxy alkyl group, with at least one of the X substituents being a hydroxy alkyl group of the structure $-(CH_2)_nOH$, wherein n is 1 to 3.

4. The complex according to claim 3 wherein said molybdenum compound is of the class consisting of molybdic trioxide, ammonium thiomolybdate, ammonium bismolybdate, molybdenum halides, and ammonium heptamolybdate tetrahydrate.

5. A lubricating oil composition comprising a major proportion of mineral oil and a minor but a friction reducing amount of an oil-soluble molybdenum complex of an ashless oxazoline lubricating oil dispersant, said dispersant having from 0.5 to 20 wt.% molybdenum based on the weight of said dispersant.

6. A hydrocarbon composition comprising a major portion of a hydrocarbon and at least a friction reducing amount of the combination of: (a) a molybdenum complex of an ashless oxazoline dispersant having from 0.5 to 20 wt.% molybdenum based on the weight of said dispersant; and (b) an oil-soluble active sulfur donor, said combination providing from about 0.01 to 2.0 weight percent molybdenum and said sulfur donor being present in at least 0.25 weight percent, all of said weight percent being based on the total weight of said composition.

7. A hydrocarbon composition according to claim 6 wherein said hydrocarbon is mineral oil, said complex is oil-soluble and derived from the reaction product of one mole of a hydrocarbyl substituted dicarboxylic acid material wherein said hydrocarbyl substituent has a ($\overline{M}_n$) ranging from 700 to 5,000 reacted with one to two moles of a 2,2-disubstituted-2-amino-1-alkanol represented by the formula

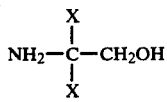

wherein X is an alkyl or hydroxy alkyl group, with at least one of the X substituents being a hydroxy alkyl group of the structure —$(CH_2)_n OH$ where n is 1 to 3, said reaction product being complexed with from 1 to 2 molar equivalents of molybdic oxide, said complex containing from 0.5 to 20 wt.% molybdenum and said sulfur donor is an oil-soluble dihydrocarbyl ester of dithiophosphoric acid.

8. A hydrocarbon composition according to claim 7 wherein said mineral oil has a viscosity as measured by ASTM D-445 of from about 2 to 40 centistokes at 99° C., said substituted dicarboxylic acid material is poly(isobutenyl) succinic anhydride wherein said poly(isobutenyl) group has a ($\overline{M}_n$) ranging from 900 to 1600, and reacted with from 1.5 to 2 moles of said alkanol, said alkanol being tris(hydroxymethyl) aminomethane and said active sulfur donor is zinc dihydrocarbyl dithiophosphate present in an amount of from 0.2 to 2 parts by weight per part by weight of said molybdenum complex which is present in an amount of from 0.02 to 1.0 wt.% based upon the total weight of said composition.

9. A concentrate comprising from 5 to 80 weight percent of the combination of an oil-soluble molybdenum complex of an ashless oxazoline dispersant having from 0.5 to 20 wt.% molybdenum based on the weight of said dispersant and from about 0.1 to 10 parts by weight of active sulfur donor per part by weight of said complex and 20 to 95 weight percent of mineral oil.

10. A method of making an oil-soluble molybdenum complex of an ashless nitrogen dispersant comprising the step of complexing a source of molybdenum with an ashless oxazoline dispersant in a binary solvent system comprising an aqueous component of the class consisting of water and ammonium hydroxide and a non-aqueous component of the class consisting of tetrahydrofuran and a hydrocarbon and the volume ratio of said aqueous component to said non-aqueous component ranging from 1:1000 to 1:1.

11. A gasoline having improved antiwear properties containing from 10 to 1,000 parts per million of a molybdenum complex of an ashless oxazoline dispersant having from 0.5 to 20 wt.% molybdenum based on the weight of said dispersant.

12. A lubricating oil composition according to claim 5 wherein said dispersant has up to 10 wt.% molybdenum.

13. A lubricating oil composition according to claim 12 wherein said dispersant is borated and contains from 0.1 to 2.0 wt.% boron based on the total weight of said dispersant.

14. A hydrocarbon composition according to claim 6 wherein said hydrocarbon is mineral oil and said molybdenum complex is oil-soluble and contains up to 10 wt.% molybdenum.

15. A concentrate according to claim 9 wherein said dispersant has up to 10 wt.% molybdenum.

16. A concentrate according to claim 15 wherein said dispersant is borated and contains from 0.1 to 2.0 wt.% boron.

17. The method according to claim 10 wherein said dispersant is borated and contains from 0.1 to 2.0 wt.% boron.

* * * * *